United States Patent [19]

Perlin

[11] Patent Number: 4,476,872
[45] Date of Patent: * Oct. 16, 1984

[54] ESOPHAGEAL PROBE WITH DISPOSABLE COVER

[75] Inventor: Alfred R. Perlin, Highland Park, Ill.

[73] Assignee: The Kendall Company, Boston, Mass.

[*] Notice: The portion of the term of this patent subsequent to Sep. 14, 1999 has been disclaimed.

[21] Appl. No.: 379,681

[22] Filed: May 12, 1982

Related U.S. Application Data

[62] Division of Ser. No. 128,323, Mar. 7, 1980, Pat. No. 4,349,031.

[51] Int. Cl.³ ............................................. A61B 5/02
[52] U.S. Cl. .................................... 128/642; 128/671; 128/696; 128/715; 128/736
[58] Field of Search ............... 128/642, 736, 696, 715, 128/786, 670, 671, 773

[56] References Cited

U.S. PATENT DOCUMENTS

| | | | |
|---|---|---|---|
| 2,949,910 | 8/1960 | Brown et al. ................... | 128/773 X |
| 3,734,094 | 5/1973 | Calmog ............................. | 128/642 |
| 3,884,219 | 5/1975 | Richardson et al. ............... | 128/736 |
| 3,951,136 | 4/1976 | Wall .................................... | 128/642 |
| 4,176,660 | 12/1979 | Mylrea ........................... | 128/736 X |
| 4,222,391 | 9/1980 | Rawson et al. ..................... | 125/736 |

OTHER PUBLICATIONS

Anesthesia & Analgesia, vol. 44, No. 1, Jan.-Feb., 1964.

*Primary Examiner*—Lee S. Cohen
*Attorney, Agent, or Firm*—Powell L. Sprunger

[57] ABSTRACT

An esophageal probe comprising, a disposable housing comprising an elongated sleeve defining a cavity, and a proximal connector. The probe has a permanent monitoring device comprising an elongated stem receivable in the sleeve cavity with a distal end of the stem located adjacent a distal end of the sleeve when the stem is fully inserted into the sleeve cavity. The monitoring device monitors a body function of a patient from a location adjacent a distal end of the stem, and has a proximal connector. The connector of the monitoring device is releasably attached to the connector of the housing when the stem is fully inserted into the sleeve cavity.

7 Claims, 5 Drawing Figures

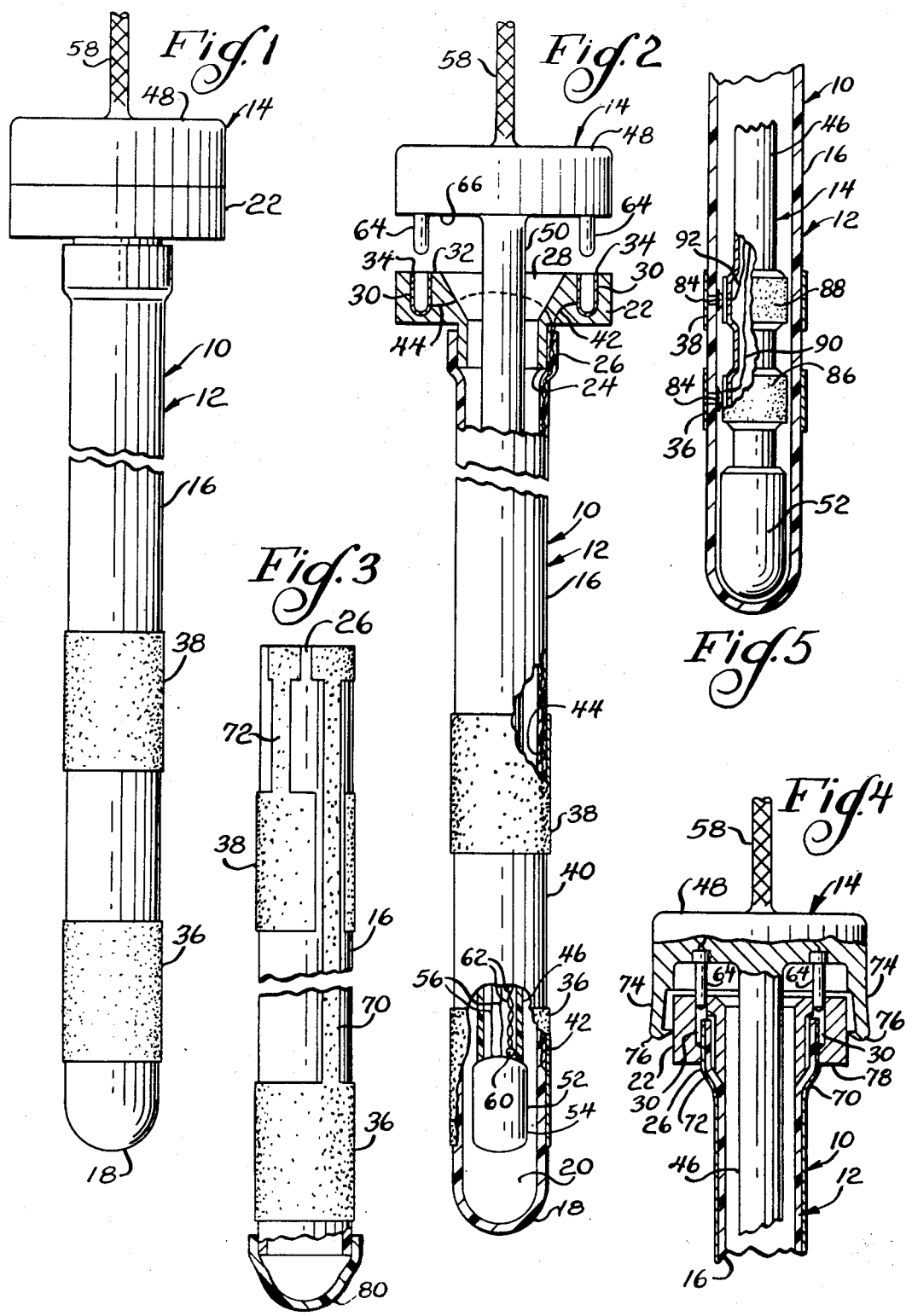

ESOPHAGEAL PROBE WITH DISPOSABLE COVER

This is a division, of application Ser. No. 128,323 filed Mar. 7, 1980, now U.S. Pat. No. 4,349,031.

BACKGROUND OF THE INVENTION

The present invention relates to monitoring devices, and more paticularly to esophageal probes.

An assortment of esophageal probes have been proposed for insertion into the esophagus of a patient to monitor body functions of the patient. However, in the past either the entire probe has been considered disposable resulting in a relatively large cost of the probe which is thrown away, or the entire probe has been considered non-disposable resulting in inconvenience of handling of the probe, such as cleaning and sterilization between uses on separate patients.

SUMMARY OF THE INVENTION

A principal feature of the present invention is the provision of an improved esophageal probe for use in a patient.

The esophageal probe of the present invention comprises, a disposable housing comprising an elongated sleeve defining a cavity, and a proximal connector. The probe has a permanent monitoring device comprising an elongated stem receivable in the sleeve cavity with a distal end of the stem located adjacent a distal end of the sleeve when the stem is fully inserted into the sleeve cavity. The monitoring device has means for monitoring a body function of a patient adjacent a distal end of the stem, and a proximal connector.

A feature of the present invention is that the connector of the monitoring device may be releasably attached to the connector of the housing when the stem is fully inserted into the sleeve cavity.

Another feature of the invention is that the disposable housing covers the stem of the monitoring device to prevent contact of the monitoring device with the patient when the probe is inserted into a patient.

Yet another feature of the invention is that the housing may be removed from the monitoring device after use in a patient, and a new housing may be attached to the monitoring device to cover the stem during use on a subsequent patient.

Further features will become more fully apparent in the following description of the embodiments of this invention and from the appended claims.

DESCRIPTION OF THE DRAWINGS

In the drawings:

FIG. 1 is a fragmentary elevational view of an esophageal probe of the present invention;

FIG. 2 is a fragmentary elevational view, taken partly in section, of the esophageal probe of FIG. 1;

FIG. 3 is a fragmentary elevational view, taken partly in section, of another embodiment of a sleeve for an esophageal probe of the present invention;

FIG. 4 is a fragmentary elevational view, taken partly in section, of a proximal end of the sleeve of FIG. 3 as incorporated in the esophageal probe of the present invention; and FIG. 5 is a fragmentary elevational view, taken partly in section, of another embodiment of the esophageal probe of the present invention.

DESCRIPTION OF THE PREFERRED EMBODIMENTS

Referring now to FIGS. 1 and 2, there is shown an esophageal probe generally designated 10 having a disposable housing or cover 12 and a permanent monitoring device 14. The housing 12 has an elongated sleeve 16 with a closed distal end 18 defining a cavity 20. The housing 12 also has an annular connector 22 having a distal annular flange 24 received in and connected to a proximal end 26 of the sleeve 16, with the connector 22 defining an opening 28 extending through the connector 22. As shown, the connector 22 has a pair of opposed recesses 30 in a proximal face 32 of the connector 22 which receive conducting sockets 34, such as metal. The sleeve 16 and connector 22 of the housing 12 may be made of any suitable material, such as plastic.

The housing 12 also has a pair of spaced cylindrical ECG electrodes 36 and 38, such as a metallic paint or metal, located on an outer surface 40 of the sleeve 16, with the electrode 36 being located adjacent the distal end 18 of the sleeve 16, and with the electrode 38 being located proximal the electrode 36. The housing 12 has a first electrical lead 42 connected to the electrode 36 and extending past the proximal end 26 of the sleeve 16 to one of the sockets 34 in the connector 22. The housing 12 also has a second electrical lead 44 connected to the electrode 38 and extending past the proximal end 26 of the sleeve 16 to the other socket 34 in the connector 22. As shown, the leads 42 and 44 may be co-extruded in the wall of the plastic sleeve 16. Alternatively, the leads 42 and 44 may be placed in an elongated recess in the wall of the sleeve 16, or may be passed through the cavity 20 in the sleeve 16 to the proximal connector 22. The connector 48 and stem 46 of the monitoring device 14 may be made of a suitable material, such as plastic.

The monitoring device 14 has an elongated stem 46 comprising a tube, and a connector 48 attached to a proximal end 50 of the stem 46. The monitoring device 14 has a vibration detection device 52, such as a microphone or hydrophone, hereinafter microphone, located at a distal end 54 of the stem 46, with suitable electrical leads 56 extending from the microphone 52 through the stem 46 and connector 48 to a cable 58 attached to the connector 48. Also, the monitoring device 14 has a temperature sensor 60 located adjacent the microphone 52 with suitable electrical leads 62 extending from the sensor 60 through the stem 46 and connector 48 to the cable 58.

As shown, the monitoring device 14 has a pair of conducting pins or posts 64, such as metal, extending from a distal face 66 of the connector 48, and being aligned with the sockets 34. Thus, the pins 64 are received in the sockets 34 to establish electrical contact between the sockets 34 and pins 64, with the monitoring device 14 having a pair of leads (not shown) electrically connected to the pins 64 and extending to the cable 58. Also, the pins 64 are frictionally engaged by the sockets 34 to releasably attach the connector 48 of the monitoring device 14 to the connector 22 of the housing 12 in a configuration with the stem 46 received in the sleeve cavity 20, and with the distal end 54 of the monitoring device 14 located adjacent the distal end 18 of the housing 12. In this manner, the monitoring device 14 may be readily attached to and removed from the disposable housing.

In use, the monitoring device 14 may be attached to a disposable housing in the manner described, and the probe 10 may be inserted into the esophagus of a patient. The cable 58 of the monitoring device 14 may be connected to suitable equipment to measure the temperature of the patient through the leads connected to the temperature sensor 60, equipment to detect heart and lung sounds through the leads connected to the microphone 52, and ECG equipment to obtain an electrocardiogram through the leads electrically connected through the pins 64 and sockets 34 to the ECG electrodes 36 and 38. After use, the probe 10 is withdrawn from the patient, the housing 12 is removed from the monitoring device 14, and the used housing 12 may be discarded. Since the housing sleeve 16 completely covers the stem 46 of the monitoring device 14, the monitoring device does not contact the patient. Thus, the monitoring device may be attached to another disposable housing 12 for use in a subsequent patient. Accordingly, the esophageal probe of the present invention permits the repeated use of the monitoring device 14 containing the expensive equipment while the housing 12 of the probe may be discarded between uses of the probe 10.

Another embodiment of the present invention is illustrated in FIGS. 3 and 4, in which like reference numerals designate like parts. In this embodiment, the electrode 36 has a conducting plate 70 such as metallic paint extending proximally from the electrode 36 on the outer surface of the sleeve 16 to the proximal end 26 of the sleeve, with the plate 70 being spaced from the electrode 38. Also, the electrode 38 has a conducting plate 72 such as metallic paint extending proximally from the electrode 38 on the outer surface of the sleeve 16 to the proximal end 26 of the sleeve 16. As shown in FIG. 4, the proximal ends of the plates 70 and 72 are positioned in the recesses 30 of the connector 22, such that the pins 64 of the monitoring device 14 contact the proximal ends of the plates 70 and 72 when the pins 64 are received in the recesses 30. In this manner, electrical connection is made between the monitoring device 14 and the electrodes 36 and 38 through the plates 70 and 72.

Also, the monitoring device 14 has a pair of flexible locking members 74 with inwardly turned distal ends 76 to releasably engage a distal face 78 of the connector 22 when the mounting device 14 is attached to the housing 12. Thus, the locking members 74 releasably lock the mounting device 14 to the housing 12, and the locking members may be pulled outwardly when it is desired to release the monitoring device 14 from the disposable housing 12. In this embodiment, the sleeve 16 comprises an elongated tube, and a suitable membrane 80, such as rubber, may be attached to the distal end of the tube in order to close the distal end of the housing 12.

Another embodiment of the present invention is illustrated in FIG. 5, in which like reference numerals designate like parts. In this embodiment, the electrodes 36 and 38 have suitable contacts 82 and 84, respectively, on the inside of the sleeve 16 which are electrically connected to the associated electrodes 36 and 38. Also, the stem 46 has a spaced pair of cylindrical conducting plates 86 and 88, respectively, disposed along the stem 46 and positioned to contact the electrode contacts 82 and 84 when the monitoring device 14 is attached to the housing 12. As shown, a pair of leads 90 and 92 are connected to the plates 86 and 88, and extend from the plates inside the stem 46 to the cable 58 at the proximal end of the monitoring device 14. In other respects, the probe 10 of FIG. 5 may be similar to the esophageal probe previously described in connection with FIGS. 1 and 2.

The foregoing detailed description is given for clearness of understanding only, and no unnecessary limitations should be understood therefrom, as modifications will be obvious to those skilled in the art.

I claim:

1. An esophageal probe, comprising:
 a disposable housing comprising an elongated sleeve defining a cavity having a proximal end, a distal end and an inner surface, said housing having a proximal opening communicating with the cavity;
 a permanent monitoring device having an elongated stem removably receivable through said opening in said sleeve cavity, said stem having a proximal end, a distal end and means for monitoring a body function of a patient from within the sleeve;
 a pair of spaced electrodes on an outer surface of the sleeve;
 means for releasably attaching said monitoring device to said housing with said stem received in the sleeve cavity; and
 means for establishing electrical connection between the electrodes and the probe monitoring device, wherein the electrical establishing means comprises a pair of spaced contacts electrically connected to the electrodes on said inner surface of the sleeve, and a pair of spaced contacts on said stem which contact the sleeve contacts when the monitoring device is attached to the housing.

2. The probe of claim 1 wherein the monitoring means comprises a vibration detection device.

3. The probe of claim 2 wherein the vibration detection device comprises a microphone.

4. The probe of claim 2 wherein the distal end of the stem is located adjacent the distal end of the sleeve when the housing is attached to the monitoring device, and in which the vibration detection device is located adjacent the distal end of the stem.

5. The probe of claim 1 wherein the stem comprises an elongated tube.

6. The probe of claim 1 wherein the distal end of the stem is located adjacent the distal end of the sleeve when the housing is attached to the monitoring device.

7. The probe of claim 1 wherein the stem contacts comprise a pair of spaced cylindrical plates.

* * * * *